(12) United States Patent
Moghaddam (10) Patent No.: US 11,253,187 B2
(45) Date of Patent: Feb. 22, 2022

(54) DEEP PERSONALIZATION BASED ON CONTEXTUAL NEUROFEEDBACK

(71) Applicant: Samsung Electronics Co., Ltd, Suwon-si (KR)

(72) Inventor: Saeed Moghaddam, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 1059 days.

(21) Appl. No.: 15/479,194

(22) Filed: Apr. 4, 2017

(65) Prior Publication Data

US 2018/0279900 A1 Oct. 4, 2018

(51) Int. Cl.
*A61B 5/375* (2021.01)
*A61B 5/00* (2006.01)
*A61B 5/316* (2021.01)

(52) U.S. Cl.
CPC ............ *A61B 5/375* (2021.01); *A61B 5/0006* (2013.01); *A61B 5/316* (2021.01); *A61B 5/7246* (2013.01); *H04M 2250/12* (2013.01)

(58) Field of Classification Search
CPC .......................... A61B 5/0482; A61B 5/0006
See application file for complete search history.

(56) References Cited

U.S. PATENT DOCUMENTS

| | | | |
|---|---|---|---|
| 2005/0177058 | A1 | 8/2005 | Sobell |
| 2013/0204153 | A1 | 8/2013 | Buzhardt |
| 2013/0207804 | A1 | 8/2013 | Li et al. |
| 2014/0347265 | A1* | 11/2014 | Aimone ............... G02C 11/10 345/156 |
| 2015/0045007 | A1 | 2/2015 | Cash |
| 2015/0092050 | A1* | 4/2015 | Cho .................... A61B 5/0482 348/143 |
| 2015/0320588 | A1* | 11/2015 | Connor ................ A61F 7/0085 607/107 |
| 2016/0135706 | A1* | 5/2016 | Sullivan ............... A61B 5/1118 600/301 |

FOREIGN PATENT DOCUMENTS

| | | |
|---|---|---|
| CN | 202682792 U | 1/2013 |
| CN | 103606245 A | 2/2014 |

\* cited by examiner

*Primary Examiner* — Daniel L Cerioni
*Assistant Examiner* — Yasmeen S Warsi (57) ABSTRACT

A method and system for operating a neural feedback system is disclosed. The method includes recording brain waves of a user, recording sensor data measuring at least one of a physical state or an activity of the user, and generating recorded context-based brain wave information by detecting correlations between the recorded brain waves and the recorded sensor data. The method further includes identifying recorded context-based brain wave patterns in the recorded context-based brain wave information and associating at least one rule of at least one electronic device with at least one recorded context-based brain wave pattern.

27 Claims, 6 Drawing Sheets

DEEP PERSONALIZATION BASED ON CONTEXTUAL NEUROFEEDBACK

TECHNICAL FIELD

This disclosure relates generally to brain wave analysis and environmental context. More specifically, this disclosure relates to systems and methods for analyzing brain waves, physical state, and environmental context and personalizing settings of an electronic device based on the analysis.

BACKGROUND

People carry portable electronic devices such as mobile phones with them on a daily basis. Users of such portable electronic devices often personalize them in various ways, both aesthetically and functionally. For example, users may set automated recurring alarms, set the phone ringer to turn off automatically during meetings scheduled on a phone calendar, or the like. As these portable electronic devices have become more advanced, the potential of personalization through automation has increased.

SUMMARY

Embodiments of the present disclosure provide systems and methods for personalizing an electronic device.

In one embodiment, a method of operating a neural feedback system is disclosed. The method includes recording brain waves of a user, recording sensor data measuring at least one of a physical state or an activity of the user, and generating recorded context-based brain wave information by detecting correlations between the recorded brain waves and the recorded sensor data. The method further includes identifying recorded context-based brain wave patterns in the recorded context-based brain wave information and associating at least one rule of at least one electronic device with at least one recorded context-based brain wave pattern.

In another embodiment, a neural feedback system is disclosed. The system includes a processor configured to record brain waves of a user, record sensor data measuring at least one of a physical state or an activity of the user, and generate recorded context-based brain wave information by detecting correlations between the recorded brain waves and the recorded sensor data. The processor is further configured to identify recorded context-based brain wave patterns in the recorded context-based brain wave information and associate at least one rule of at least one electronic device with at least one recorded context-based brain wave pattern.

In yet another embodiment, a non-transitory computer readable medium embodying a computer program is disclosed. The computer program includes computer readable program code that when executed causes at least one processor to record brain waves of a user, record sensor data measuring at least one of a physical state or an activity of the user, and generate recorded context-based brain wave information by detecting correlations between the recorded brain waves and the recorded sensor data. The program code when executed further causes the at least one processor to identify recorded context-based brain wave patterns in the recorded context-based brain wave information and associate at least one rule of at least one electronic device with at least one recorded context-based brain wave pattern.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 6, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Embodiments of the present disclosure recognize and take into account that different types of brain waves are associated with different mental or intellectual states. For example, Delta waves may indicate that a person is sleepy. Theta waves may indicate that a person is visualizing something in their mind. Beta waves may indicate that a person is thinking or trying to solve a problem. By analysis of brain waves it is possible to detect complex mental and intellectual states such as excitement, engagement, boredom, meditation, concentration, and frustration. Brain wave detection devices may interface with portable electronic devices such as mobile phones to provide mobile brain wave detection.

Portable electronic devices such as mobile phones may also contain a suite of sensors and can be a source of information about the user's environmental context. For example, a mobile phone can provide information on the time of day, the user's location, their travel speed, the weather around the user, or whether the user is currently using any applications on the device. It may be desirable to use brain wave detection and information about the user's environmental context to provide personalization or recommendation of the settings of an electronic device.

Accordingly, embodiments of the present disclosure provide systems and methods for fusion of brain wave information and sensed environmental context information to create rules for personalization of the settings of one or more electronic devices, or rules for providing recommendations for settings of one or more electronic devices. For example, embodiments of the present disclosure describe recording brain wave and contextual environmental context information, correlating the brain wave and contextual environmental context information to determine the mental reactions of a user to environmental stimuli, and use that determination to form rules for modifying the settings of one or more electronic devices to modify the environment of the user to induce desired mental reactions.

Embodiments of the present disclosure also provide systems and methods for receiving real time brain wave and contextual environmental context information, correlating the real time brain wave and contextual environmental context information, and using that information to search for rules that will modify the environment of the user to induce desired mental reactions.

Figure 1:
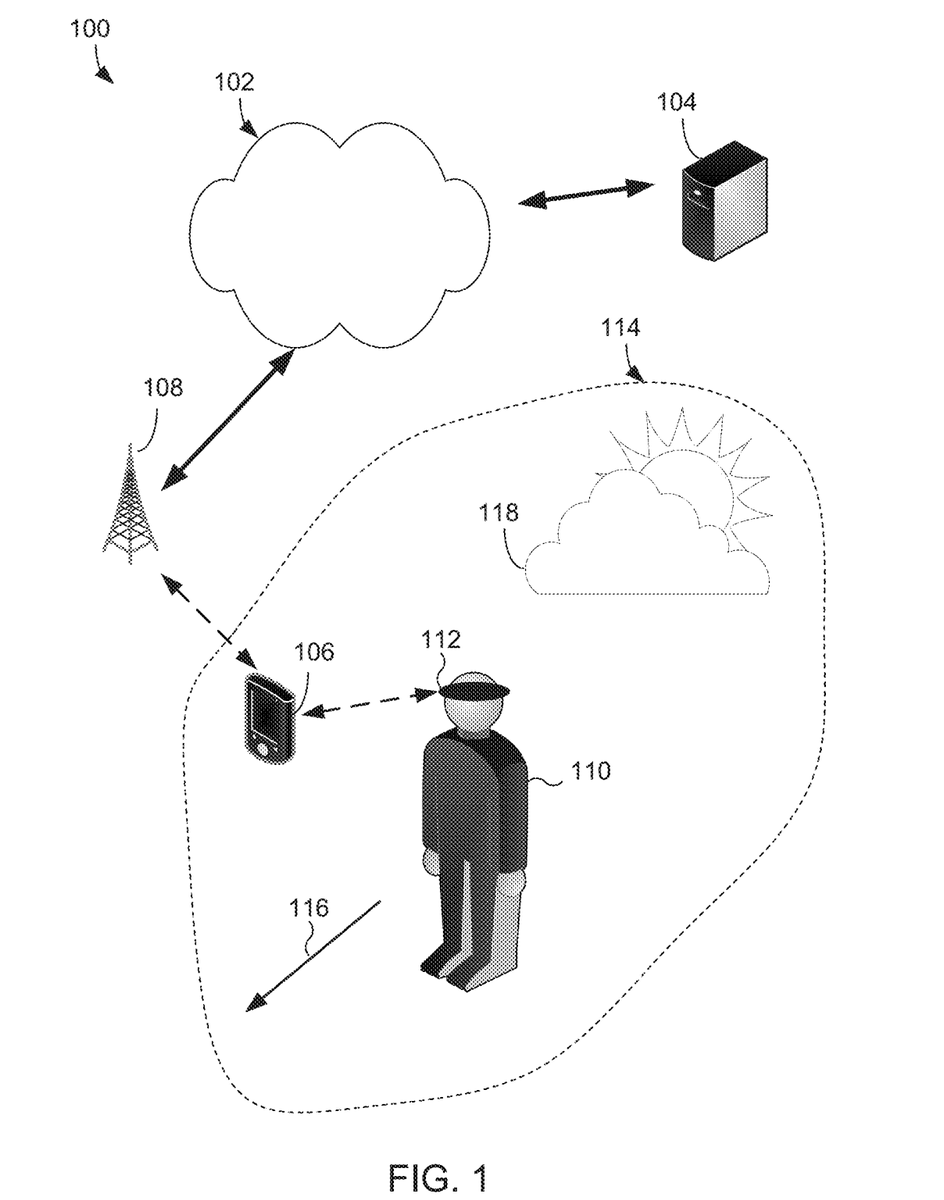
FIG. 1 illustrates an example computing system according to illustrative embodiments of the present disclosure.

FIG. 1 illustrates an example computing system 100 according to this disclosure. The embodiment of the computing system 100 shown in FIG. 1 is for illustration only. Other embodiments of the computing system 100 could be used without departing from the scope of this disclosure.

As shown in FIG. 1, the system 100 includes a network 102, which facilitates communication between various components in the system 100. For example, the network 102 may communicate Internet Protocol (IP) packets, frame relay frames, Asynchronous Transfer Mode (ATM) cells, or other information between network addresses. The network 102 may include one or more local area networks (LANs), metropolitan area networks (MANs), wide area networks (WANs), all or a portion of a global network such as the Internet, or any other communication system or systems at one or more locations.

The network 102 may facilitate communications between at least one server 104 and personal electronic devices such as smartphone 106 or scanning device 112. Each server 104 includes any suitable computing or processor that can provide computing services for one or more personal electronic devices. Each server 104 could, for example, include one or more processors, one or more memories storing instructions and data, and one or more network interfaces facilitating communication over the network 102.

The smartphone 106 may be any suitable computing or processing device that interacts with at least one server or other computing device(s) over the network 102. The smartphone 106 could alternatively be a desktop computer, a personal digital assistant (PDA), a laptop computer, or a tablet computer. Any other or additional electronic devices could be used in the computing system 100.

In this example, the smartphone 106 communicates indirectly with the network 102. For example, the smartphone 106 communicates via one or more base stations 108, such as cellular base stations or eNodeBs. In other embodiments, the smartphone 106 may communicate via wireless access points, such as IEEE 802.11 wireless access points. Note that these are for illustration only and that the smartphone 106 could communicate directly with the network 102 or indirectly with the network 102 via any suitable intermediate device(s) or network(s).

The system 100 further includes a user 110 wearing a scanning device 112. In this example, the scanning device 112 includes one or more sensors capable of monitoring or recording brain waves of the user 110 and of measuring facial muscle movement, for example by electroencephalography. The scanning device 112 may communicate directly with the smartphone 106, thereby providing the smartphone 106 with access to the neural information gathered by the scanning device 112 about the user 110. In other embodiments, the scanning device 112 may communicate directly or indirectly with the server 104, thereby providing the server 104 with access to the neural information gathered by the scanning device 112.

FIG. 1 also includes a conceptual illustration of the user's environment 114. The environment 114 includes various pieces of environmental information, such as the user's velocity or acceleration 116, the weather or inside temperature conditions 118, the time of day, the user's geographical location, functions of the smartphone 106 such as running applications, music that is playing, and the like, and functions of other electronic devices such as smart vehicle systems (e.g., audio system, climate control system). The environmental information may, in some embodiments, be gathered by sensors in the smartphone 106. In other embodiments, sensors in the scanning device 112 or external sensors in communication with the smartphone 106 or the scanning device 112 may gather some or all of the environmental information.

In some embodiments, the environmental information and the neural information gathered by the smartphone 106 and the scanning device 112 are communicated to the server 104 by the smartphone 106 for analysis. In this case, the server 104 may contain a contextual neurofeedback unit. In some embodiments, the environmental information and the neural information gathered by the smartphone 106 and the scanning device 112 are analyzed by the smartphone 106, which may contain a contextual neurofeedback unit.

As described in more detail below, analysis of the environmental information and the neural information gathered by the smartphone 106 and the scanning device 112 may be used to correlate the user 110's mental and physical state to environmental conditions and to modify the behavior of the smartphone 106 or other electronic devices in the user 110's environment 114 based on the user 110's current or desired mental and physical state.

Although FIG. 1 illustrates one example of a computing system 100, various changes may be made to FIG. 1. For example, the system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

Figure 2:
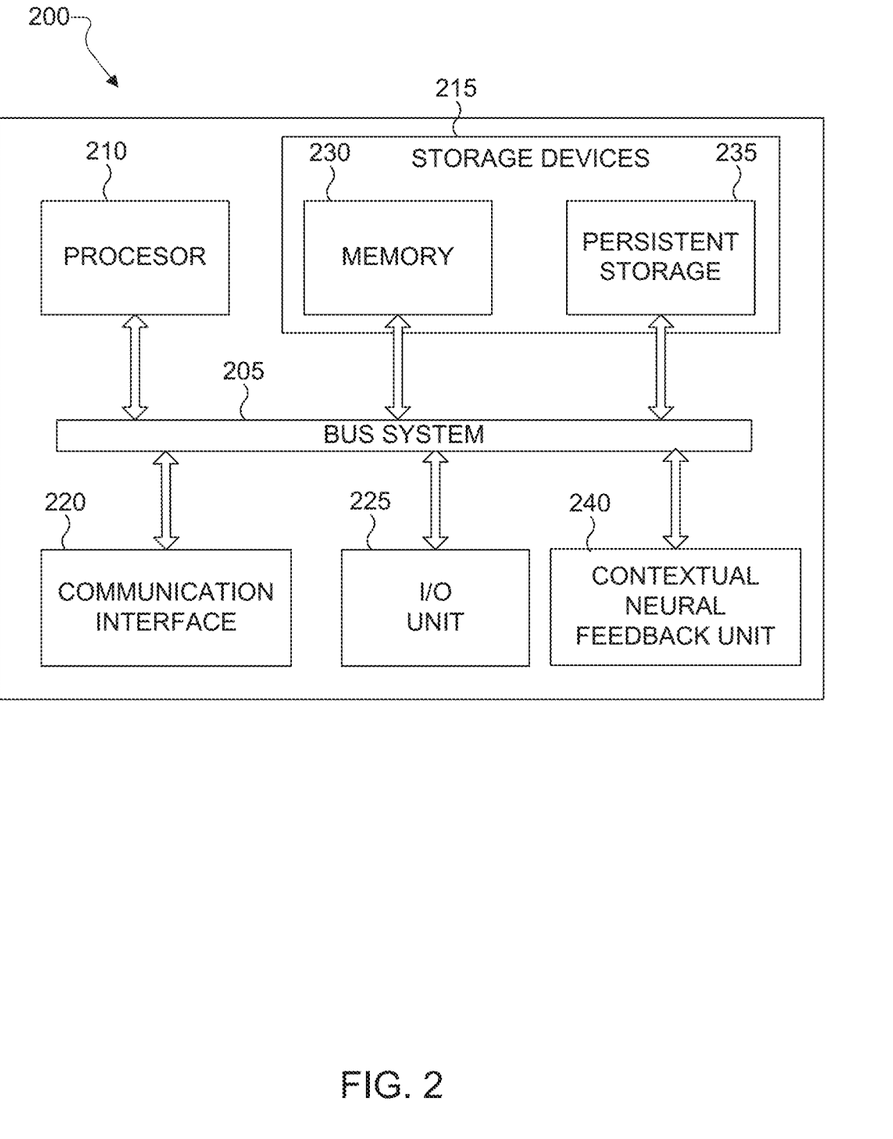
FIG. 2 illustrates an example server according to illustrative embodiments of the present disclosure.
Figure 3:
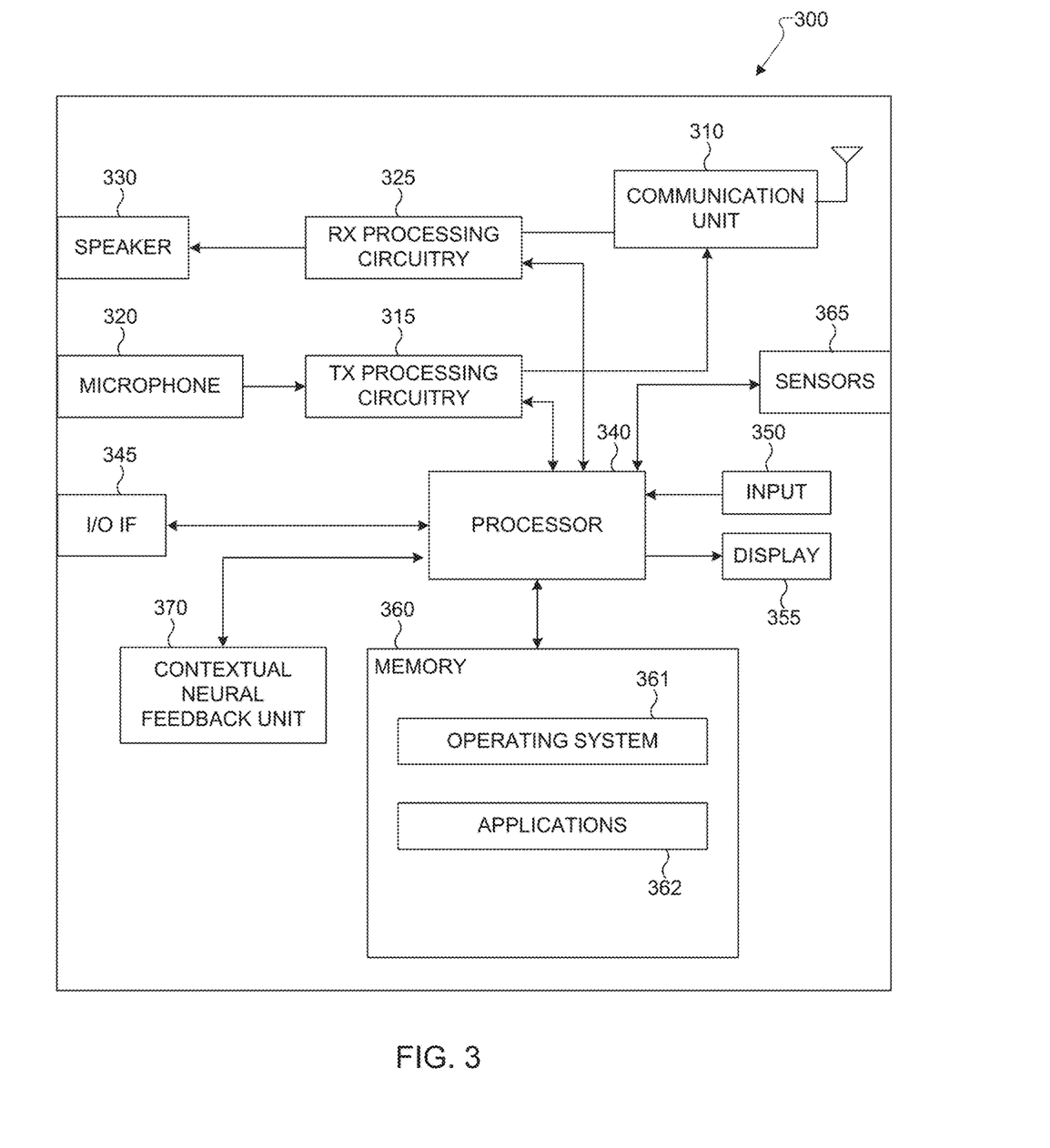
FIG. 3 illustrates an example electronic device according to illustrative embodiments of the present disclosure.

FIGS. 2 and 3 illustrate example devices in a computing system according to this disclosure. In particular, FIG. 2 illustrates an example computer system 200, and FIG. 3 illustrates an example electronic device 300. The computer system 200 could represent the server 104 in FIG. 1, and the electronic device 300 could represent the smartphone 106 or the scanning device 112 in FIG. 1.

As shown in FIG. 2, the computer system 200 includes a bus system 205, which supports communication between at least one processor 210, at least one storage device 215, at least one communication interface 220, and at least one input/output (I/O) unit 225.

The processor 210 executes instructions that may be loaded into a memory 230. The processor 210 may include any suitable number(s) and type(s) of processors or other devices in any suitable arrangement. Example types of processors 210 include microprocessors, microcontrollers, digital signal processors, field programmable gate arrays, application specific integrated circuits, and discreet circuitry.

The memory 230 and a persistent storage 235 are examples of storage devices 215, which represent any structure(s) capable of storing and facilitating retrieval of information (such as data, program code, and/or other suitable information on a temporary or permanent basis). The memory 230 may represent a random access memory or any other suitable volatile or non-volatile storage device(s). The persistent storage 235 may contain one or more components or devices supporting longer-term storage of data, such as a read only memory, hard drive, Flash memory, or optical disc.

The communication interface 220 supports communications with other systems or devices. For example, the communication interface 220 could include a network interface card or a wireless transceiver facilitating communications over the network 102. The communication interface 220 may support communications through any suitable physical or wireless communication link(s).

The I/O unit 225 allows for input and output of data. For example, the I/O unit 225 may provide a connection for user input through a keyboard, mouse, keypad, touchscreen, or other suitable input device. The I/O unit 225 may also send output to a display, printer, or other suitable output device.

The contextual neurofeedback unit 240 analyzes data gathered by the smartphone 106 or the scanning device 112, as will be described in more detail below. This information may be received from the smartphone 106 via the communication interface 220 and the bus system 205. The results of the analysis may be returned to the smartphone 106 via the bus system 205 and the communication interface 220. As will be discussed in greater detail below, the computer system 200 can receive recorded user brain waves and recorded sensor data and generate rules and recommendations.

Note that while FIG. 2 is described as representing the server 104 of FIG. 1, the same or similar structure could be used in the smartphone 106 or any other computing device in system 100. For example, a smart vehicle or laptop computer could have the same or similar structure as that shown in FIG. 2.

As shown in FIG. 3, the electronic device 300 includes a communication unit 310, transmit (TX) processing circuitry 315, a microphone 320, and receive (RX) processing circuitry 325. The communication unit 310 may include, for example, a radio frequency (RF) transceiver, a Bluetooth® transceiver, or a WiFi transceiver. The electronic device 300 also includes a speaker 330, a processor 340, an input/output (I/O) interface (IF) 345, an input interface 350, a display 355, a memory 360, sensors 365, and a contextual neurofeedback unit 370. The memory 360 includes an operating system (OS) program 361 and one or more applications 362.

The communication unit 310 may receive an incoming RF signal such as a Bluetooth® or WiFi signal. The communication unit 310 may down-convert the incoming RF signal to generate an intermediate frequency (IF) or baseband signal. The IF or baseband signal is sent to the RX processing circuitry 325, which generates a processed baseband signal by filtering, decoding, and/or digitizing the baseband or IF signal. The RX processing circuitry 325 transmits the processed baseband signal to the speaker 330 (such as for voice data) or to the processor 340 for further processing (such as for web browsing data). The processor 340 may further transmit the processed baseband signal to the contextual neurofeedback unit 370 for further processing (such as for environmental and neural information).

In some embodiments, the communication unit 310 may be a short range wireless communications transceiver that implements a wireless communications protocol such as Bluetooth®, Wi-Fi Direct®, or NFC. In such embodiments, the communication unit 310 may include any hardware or software necessary for sending and receiving the short range signals. In other embodiments the communication unit 310 may facilitate both long range and short range communications using any appropriate communications protocols. For example, a smartphone 106 may use a cellular communications protocol to communicate via network 102 with server 104 and additionally may use a short range communications protocol to communicate with scanning device 112.

The TX processing circuitry 315 receives analog or digital voice data from the microphone 320 or other outgoing baseband data (such as web data, e-mail, or interactive video game data) from the processor 340. The TX processing circuitry 315 encodes, multiplexes, and/or digitizes the outgoing baseband data to generate a processed baseband or IF signal. The communication unit 310 receives the outgoing processed baseband or IF signal from the TX processing circuitry 315 and, in the case that the communication unit 310 is an RF transceiver, up-converts the baseband or IF signal to an RF signal that is transmitted via an antenna.

The processor 340 can include one or more processors or other processing devices and execute the OS program 361 stored in the memory 360 in order to control the overall operation of the electronic device 300. For example, the processor 340 could control the reception of forward channel signals and the transmission of reverse channel signals by the communication unit 310, the RX processing circuitry 325, and the TX processing circuitry 315 in accordance with well-known principles. In some embodiments, the processor 340 includes at least one microprocessor or microcontroller.

The processor 340 is also capable of executing other processes and programs resident in the memory 360. The processor 340 can move data into or out of the memory 360 as required by an executing process. In some embodiments, the processor 340 is configured to execute the applications 362 based on the OS program 361 or in response to signals received from external devices or an operator. The processor 340 is also coupled to the I/O interface 345, which provides the electronic device 300 with the ability to connect to other devices such as laptop computers and handheld computers. The I/O interface 345 is the communication path between these accessories and the processor 340.

The processor 340 is also coupled to the input interface 350 and the display 355. The operator of the electronic device 300 can use the input interface 350 to enter data into the electronic device 300. The display 355 may be a liquid crystal display or other display capable of rendering text and/or at least limited graphics, such as from web sites.

The memory 360 is coupled to the processor 340. Part of the memory 360 could include a random access memory (RAM), and another part of the memory 360 could include a Flash memory or other read-only memory (ROM).

The sensors 365 detect information external to the electronic device 300 and relay it to the processor 340 for further processing. For example, in a smartphone 106 the sensors 365 may detect motion, light level, ambient temperature, heart rate of a user 110, and the like. In some embodiments of a smartphone 106, external sensors may be connected to the smartphone 106 alongside internal sensors 365. In a scanning device 112, the sensors 365 may detect brain waves of a user 110, for example via an electroencephalograph (EEG).

The contextual neurofeedback unit 370 analyzes data gathered by the smartphone 106 and the scanning device 112, for example data gathered by sensors 365, as will be described in more detail below. The contextual neurofeedback unit 370 is coupled to the processor 340. In some embodiments, the processor 340 may provide processing power to the contextual neurofeedback unit 370. In some embodiments, the processor 340 may pre-process the environmental and neural information gathered by the sensors 365 or received through the communication unit 310 before transmitting it to the contextual neurofeedback unit 370. As will be discussed in greater detail below, the electronic device 300 can receive recorded user brain waves and recorded sensor data and generate rules and recommendations.

Although FIGS. 2 and 3 illustrate examples of devices in a computing system, various changes may be made to FIGS. 2 and 3. For example, various components in FIGS. 2 and 3 could be combined, further subdivided, or omitted and additional components could be added according to particular needs. As a particular example, the processor 340 could be divided into multiple processors, such as one or more central processing units (CPUs) and one or more graphics processing units (GPUs). Also, while FIG. 3 illustrates the electronic device 300 configured as a smartphone or scanning device, electronic devices could be configured to operate as other types of mobile or stationary devices. In addition, as with computing and communication networks, electronic devices and servers can come in a wide variety of configurations, and FIGS. 2 and 3 do not limit this disclosure to any particular client device or server.

Figure 4:
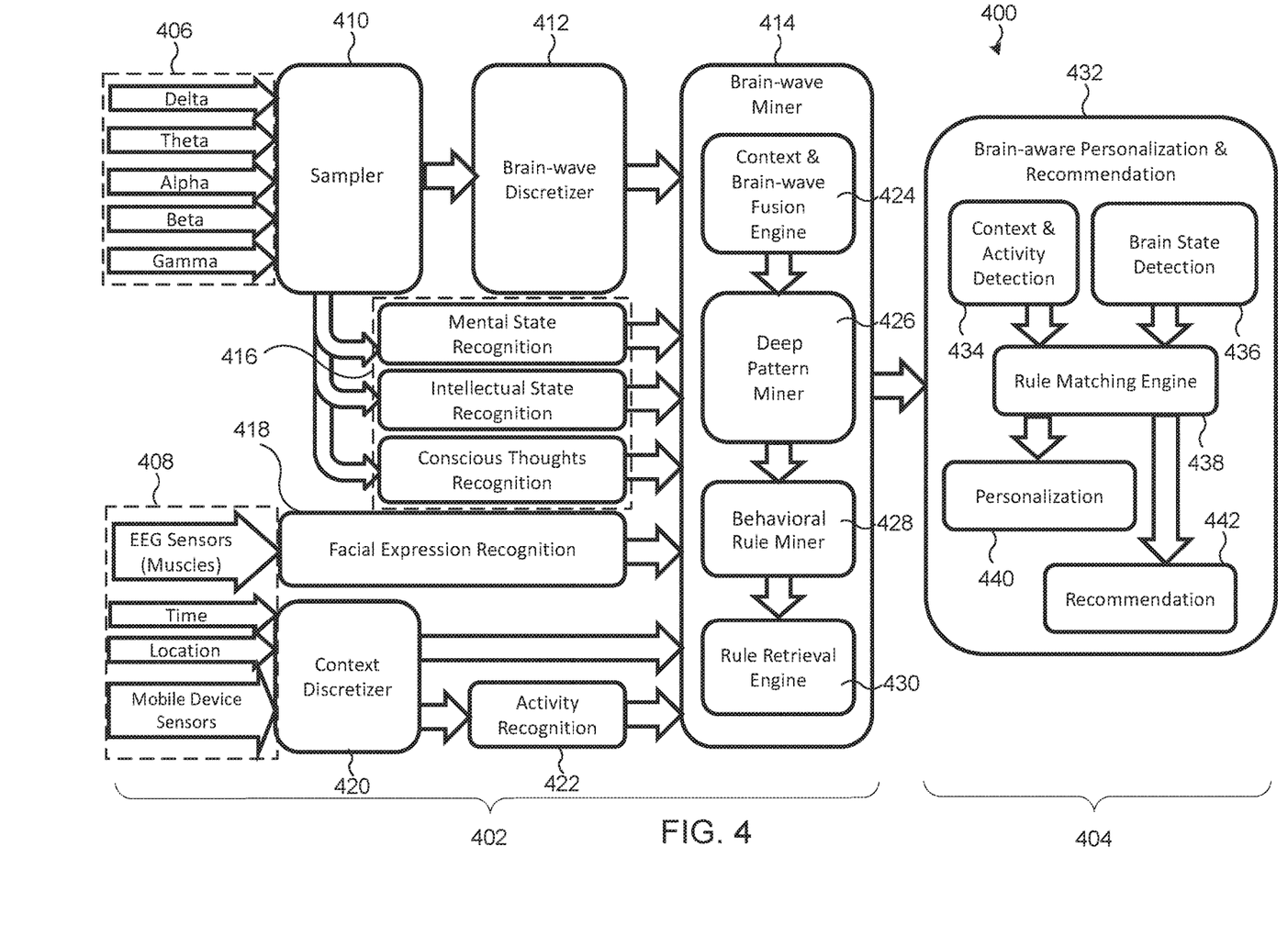
FIG. 4 illustrates an example contextual neurofeedback system according to illustrative embodiments of the present disclosure.

FIG. 4 illustrates an example contextual neurofeedback system 400 according to illustrative embodiments of the present disclosure. The contextual neurofeedback system 400 may, for example, be a contextual neurofeedback unit 240 of FIG. 2 or a contextual neurofeedback unit 370 of FIG. 3. For example, in some embodiments, the contextual neurofeedback system 400 may be located in a single device or system, such as, for example, electronic device 300 or the computer system 200. In other embodiments, elements of the contextual neurofeedback system 400 may be distributed over multiple devices or systems.

In this embodiment the contextual neurofeedback system 400 is used to analyze environmental and neural information related to a user 110 to detect both simple and complex mental and intellectual states of the user 110 and to detect different types of conscious thought of the user 110, to detect facial expressions of the user 110, and to combine this information to generate or form contextual neural patterns associated with the user 110.

The contextual neurofeedback system 400 includes a modeling portion 402 and a real time brain aware personalization and recommendation portion 404. As will be further described below, the modeling portion 402 records and analyzes environmental and neural information in a first timeframe to build a contextual neurofeedback model, and the real time brain aware personalization and recommendation portion 404 applies the contextual neurofeedback model to environmental and neural information gathered in real time to personalize the functions of one or more electronic devices based on the contextual neurofeedback model. The portions may be implemented together in a single unit or distributed across multiple units.

As described above, the contextual neurofeedback system 400 receives neural information 406 and environmental information 408 from sensors in an electronic device such as scanning device 112 or smartphone 106 during a first timeframe. Neural information 406 includes, for example, the brain waves of the user 110, which may be Delta, Theta, Alpha, Beta, and Gamma waves. The different classifications of brain waves represent patterns of electrical activity in the human brain that are known to represent different mental and intellectual states. For example, Beta waves are characteristic of a highly engaged mental state, which might occur during active critical thought. Beta waves are detected by an EEG as a rapidly varying, relatively low voltage electrical signal in the brain. Delta waves are, on the other hand, characteristic of a very relaxed and disengaged mental state, such as might occur during dreamless sleep. Delta waves are detected by an EEG as a slowly varying, relatively high voltage electrical signal in the brain. The neural information 406 is fed into a sampler 410. In some embodiments, the environmental information 408 is also fed into the sampler 410.

The sampler 410 may save resources by dynamically adjusting a sampling rate of the neural information 406 based on the type of brain waves that are sensed from the user 110. For example, while the user 110 is outputting low frequency, slowly changing Delta waves, the sampler 410 may lower its sampling rate to save resources (e.g., memory) while still capturing all changes in brain state. Similarly, while the user 110 is outputting high frequency, rapidly changing Beta waves, the sampler 410 may increase its sampling rate to ensure that all changes in brain state are captured.

In some embodiments, the sampler 410 may also receive environmental information 408 from an electronic device 300. For example, the electronic device 300 may provide the time of day to the sampler 410. In this example, the sampler 410 may use learning algorithms to track a user 110's sleep schedule, and may learn the approximate times that the user 110 is in the various phases of sleep, such as dreamless sleep and rapid eye movement (REM) sleep. The sampler 410 may be pre-programmed with average sleep cycle lengths, and may adaptively learn when the user 110 typically goes to sleep. The sampler 410 may thereby estimate the types of brain waves that it will receive at a given time based on its knowledge of average sleep cycle lengths. Dreamless sleep is typically characterized by Delta waves, while REM sleep is typically characterized by Theta waves. If an average person enters REM sleep after 90 minutes and the sampler 410 learns that the user 110 typically goes to sleep at 10:00 PM, the sampler 410 may estimate that at 11:30 it should expect to begin receiving Theta waves, and it may gradually increase its sampling rate in anticipation of the increase in frequency of change of brain waves.

In some embodiments, the sampler 410 may be pre-programmed with information pertaining to the expected brain activity of an average person, but may learn a user 110's specific patterns of brain activity over time. In this way, the sampler 410 may learn over time what neural information to expect to receive based on the environmental information that it receives, thereby increasing its efficiency by predicting changes in brain activity before they occur and proactively adjusting its sampling rate. However, even without such learning capabilities (or before the sampler 410 has had sufficient time to learn), the sampler 410 is able to measure changes in frequency of brain waves and adjusting its sampling rate reactively.

The sampler 410 may send the sampled neural information that it generates to a brain wave discretizer 412. The brain wave discretizer 412 bins the efficiently sampled neural information from the sampler 410 into a predetermined number of discrete levels. For example, if the voltage level of the efficiently sampled neural information is between 70 mV and 100 mV, the brain wave discretizer 412 may bin the neural information into seven 5 mV bins. This allows some tradeoff between fidelity of information and storage resources. The higher the number of bins used by the brain wave discretizer 412, the higher the fidelity of the information to the original signal, but the more storage space is used to store the discretized neural information. The brain wave discretizer 412 transmits the discretized neural information to the brain wave miner 414 for further processing as described below.

Returning to the sampler 410, the efficiently sampled neural information may also be passed to brain state analysis module 416, which may recognize the mental state, the intellectual state, and the conscious thoughts of the user 110. This may be appropriate if the brain state analysis module 416 performs analog processing. Alternatively, the brain state analysis module 416 may receive its inputs from the brain wave discretizer 412 if appropriate, for example if the modules perform digital processing.

The brain state analysis module 416 analyzes neural information over time to detect mental and intellectual states such as excitement, engagement, boredom, meditation, concentration, and frustration. The brain state analysis module 416 also is able to detect various conscious thought patterns, such as conscious thought about movement, rotation, or visualization. Detected mental and intellectual state information is transmitted by the brain state analysis module 416 to the brain wave miner 414 for further processing as described below.

A facial expression recognition module 418 receives EEG signals (part of environmental information 408) from an EEG, which may be included in an electronic device such as smartphone 106 or scanning device 112, or an external sensor connected to the electronic device 300. The facial expression recognition module analyzes the EEG information to detect facial expressions of the user 110 such as smiling, frowning, laughing, eye position, eyebrow position, eyelid position, or the like. Detected facial expression information is transmitted by the facial expression recognition module 418 to the brain wave miner 414 for further processing as described below.

A context discretizer 420 receives environmental information 408 from the electronic device 300, for example from sensors and applications. The context discretizer 420 bins the environmental information 408 into a predetermined number of discrete levels. The higher the number of bins used by the context discretizer 420, the higher the fidelity of the information to the original signal, but the more storage space is required. The context discretizer 420 transmits the discretized neural information to the brain wave miner 414 for further processing as described below, as well as to an activity recognition module 422.

The activity recognition module 422 combines the pieces of environmental information 408 and analyzes it to deduce the user 110's activity. For example, the activity recognition module 422 may deduce based on location (e.g., on a major road), that the user 110 is driving, and may further deduce based on time of day (e.g., 5:30 PM), and velocity (e.g., 30 miles per hour), that the user is driving home in rush hour traffic. In some embodiments, the activity recognition module 422 may learn over time the user 110's behavior in order to refine its deductions. For example, the activity recognition module 422 may learn that the user 110 generally commutes from work to home at 8:00 PM, and accordingly does not encounter rush hour traffic. As a result, the activity recognition module 422 may deduce based only on the fact that the user 110's location is located on a specific road between 8:00 PM and 9:00 PM that the user is driving home. The activity recognition module 422 transmits the activity information that it generates to the brain wave miner 414 for further processing as described below.

The brain wave miner 414 includes various hardware to perform various functions, including a context and brain wave fusion engine 424, a deep pattern miner 426, a behavioral rule miner 428, and a rule retrieval engine 430. The brain wave miner 414 receives all of the recorded and processed information described above, further processes it as described below, and communicates with a brain-aware personalization and recommendation engine 432 in order to facilitate real time personalization of one or more devices such as electronic device 300.

The context and brain wave fusion engine 424 accounts for any difference in sampling rate between various pieces of neural information due to the sampler 410. The context and brain wave fusion engine 424 additionally associates environmental information with neural information. For example, neural information and environmental information recorded during a same timeframe may be associated by the context and brain wave fusion engine 424 so that the environmental information provides context for the neural information. The resulting information may be referred to as contextual neural information.

The deep pattern miner 426 analyzes the contextual neural information to look for patterns. A user 110 may have similar reactions to similar sets of stimuli in the environment, for example, across multiple days the user 110 may be frustrated and bored while commuting home in rush hour traffic. The deep pattern miner 426, analyzing contextual neural information collected over a period of several days or weeks, determines that when the user 110's environmental information shows roughly 20 mile per hour movement on a major road between 5:30 and 6:30 PM on a weekday (i.e., while user 110 is commuting home during rush hour traffic), the user's neural information and facial expression information indicates frustration and boredom. This contextual neural pattern is stored and transmitted to the behavioral rule miner 428.

The behavioral rule miner 428 uses contextual neural patterns detected by the deep pattern miner 426 to create rules of behavior for one or more electronic devices 300, or other devices in the user 110's environment 114, in order to elicit desired responses in the user 110. Rules of behavior will be referred to simply as rules below. These desired responses of user 110 may also be determined based on patterns detected by the deep pattern miner 426. For example, the deep pattern miner 426 may determine that reducing the ambient temperature in environment 114 and playing high tempo music causes the user 110 to enter an excited and happy mental state, and may determine that this is beneficial when the user 110 is determined to be driving. Such a determination may be made by consulting a source of outside information, such as a database containing desirable mental states for average users with similar contextual neural patterns.

Accordingly, the behavioral rule miner 428 may create the following rule: If movement speed is between 20-30 miles per hour, time of day is between 5:30 and 6:30 PM, location is on a major road, and mental state is frustrated or bored, then cause vehicle climate control system to reduce temperature (e.g., to 68 degrees Fahrenheit) and cause smartphone 106 or vehicle audio system to play high tempo music.

In other embodiments, the behavioral rule miner 428 creates a rule to complement the mental and physical state of the user. For example, the behavioral rule miner 428 may determine from contextual neural patterns an optimal temperature at which a user 110 enters a state of relaxation or sleepiness, and may determine that low tempo music also causes the user 110 to enter the state of relaxation or sleepiness. The behavioral rule miner 428 may determine that it is desirable for the user to enter this state of relaxation at night time while at home. Accordingly, the behavioral rule miner 428 creates the following rule: if the time of day is after 8:00 PM, the user is located at home, and the user's brain waves indicate a state of relaxation, then adjust the home thermostat to an optimal temperature for sleep and cause the smartphone 106 or a home stereo system to play low tempo music.

People do not always react the same way to the same stimuli, and accordingly a result associated with a contextual neural pattern may not be reproducible 100% of the time. Accordingly, in some embodiments, the deep pattern miner 426 and the behavioral rule miner 428 collaborate to determine a confidence level of a result of the "if-then" rule. For example, based on multiple instances of the user 110 driving with the vehicle air temperature in a temperature range of 65-70 degrees Fahrenheit with high tempo music playing, the behavioral rule miner 428 may determine that 70% of the time the user is put in an excited and happy mental state. These rules and associated confidence levels of results are stored for retrieval by the rule retrieval engine 430.

In some embodiments, the behavioral rule miner 428 stores created rules in a memory, such as one of storage devices 215 of computer system 200 or memory 360 of electronic device 300, for later use. The stored rules may be accessed, for example, by the rule retrieval engine 430, as will be described below.

The rule retrieval engine 430 communicates with the brain-aware personalization and recommendation engine 432 to facilitate enactment of the rules by electronic devices 300, or other devices, in the user 110's environment 114. As will be further described below, the brain-aware personalization and recommendation engine 432 via a rule matching engine 438 provides real time information about the user 110's brain state and environmental context in the form of real time neural and environmental information. The rule retrieval engine 430 uses this real time information to select an appropriate rule to achieve a desired resulting mental and physical state in the user 110. In other embodiments, a rule may be selected to complement a user's current mental and physical state, for example by further relaxing a user 110 that is entering a state of relaxation.

In some embodiments, desired results are pre-programmed into the rule retrieval engine 430 by the user 110 for specific situations. For example, a user 110 may consult the recorded contextual neural patterns to determine that he or she often enters a state of boredom and frustration while commuting in rush hour traffic, and may then decide to pre-program the electronic device 300 to select a rule that will put him into a mental state more conducive to driving (e.g., excited, happy, or focused) when those contextual neural patterns are detected. In another example, the user 110 may pre-program the electronic device 300 to search for a rule that will put the user into a mental state of relaxation when the electronic device 300 detects contextual neural patterns that indicate that the user 110 is settling in for the evening at home.

In some embodiments, the rule retrieval engine 430 determines a desired result autonomously. The rule retrieval engine 430 may, for example, communicate with an external database of suggested results for given contextual neural patterns. For instance, the external database may, based on multiple users 110, indicate that it is desirable for users 110 who are driving while frustrated or bored to be put into an excited and happy state. Accordingly, the rule retrieval engine 430 may choose the appropriate rule for the specific user 110 that has the highest confidence level of putting the user into an excited and happy state when it is determined that the user is driving while frustrated or bored.

The brain-aware personalization and recommendation engine 432 performs real time monitoring of neural and environmental information corresponding to a user 110 and communicates with the rule retrieval engine 430 of the brain wave miner 414 to suggest to the user 110 or to automatically enact various rules of behavior of one or more electronic devices 300, or of other devices in the environment 114, in an attempt to change the user's mental and physical state. The brain-aware personalization and recommendation engine 432 includes a context and activity detection module 434, a brain state detection module 436, a rule matching engine 438, a personalization module 440, and a recommendation module 442.

The context and activity detection module 434 functions similarly to the activity recognition module 422 and the facial expression recognition module 418 in real time. The context and activity detection module 434 receives real time environmental information related to environment 114 from sensors in one or more electronic devices 300 (such as smartphone 106). The context and activity detection module 434 may transmit this environmental information directly to the rule matching engine 438, or may further process the environmental information into activity information. For example, the context and activity detection module 434 may receive velocity information of 25 miles per hour, time of day information indicating that it is 5:45 PM on Wednesday, and location information indicating that the user 110 is traveling on a major road. The context and activity detection module 434 determines that the user 110's current activity is driving in rush hour traffic, and transmits this information to the rule matching engine 438.

The brain state detection module 436 functions similarly to the brain state analysis module 416 in real time. The brain state detection module 436 receives real time neural information of the user 110 from sensors in one or more electronic devices 300 (such as the scanning device 112). The brain state detection module 436 may transmit this neural information directly to the rule matching engine 438, or may further process the neural information into brain state information. For example, the brain state detection module 436 determines from real time brain waves that the user is frustrated and bored, and transmits this information to the rule matching engine 438.

Rule matching engine 438 determines a real time environmental and neural context for the user 110 and communicates with the rule retrieval engine 430 to determine whether to modify the behavior of any electronic devices 300, or other devices, in the environment 114 in an attempt to modify the brain state of the user 110. In some embodiments, some of the features described above with respect to the rule retrieval engine 430 (e.g., determining a desired result) may be included in the rule matching engine 438. Once a rule has been selected and retrieved from the rule retrieval engine 430, the rule matching engine 438 transmits the rule to the personalization module 440 or the recommendation module 442, depending on settings predetermined by the user 110.

Personalization module 440 receives the selected rule and modifies the settings of one or more electronic devices 300, or other devices, in the environment 114 according to the rule. For example, personalization module 440 causes the user 110's vehicle climate control system to lower the temperature (e.g., to 68 degrees Fahrenheit), and to play a high tempo song.

Recommendation module 442 functions similarly to personalization module 440, except that the behavior according to the rule is recommended to the user 110 rather than automatically enacted. For example, the user 110's smartphone 106 may alert the user 110 that it has detected that user 110 is bored or frustrated and driving in traffic, and suggest that user 110 lower the air temperature and play high tempo music. The smartphone 106 may leave it to the user 110 to take the recommended action, or may ask the user 110 if the user 110 would like the smartphone 106 to facilitate the recommended actions. In another example, the user 110's smartphone 106 may detect that the user 110 is located at home at during the evening (e.g., between 8:00 and 10:00 PM), and that the user is in a relaxed state of mind, and suggest a selection of movies, music, or other media to play that are relaxing.

In some embodiments, the brain wave miner 414 may periodically update rules based on new information gathered by the contextual neurofeedback system 400 or by the brain-aware personalization and recommendation engine 432. For example, when the context and activity detection module 434 and the brain state detection module 436 receive information, that information may be communicated to the brain wave miner 414, which may use the information to generate new rules as described above. In another example, the brain wave miner 414 may periodically receive new neural information 406 and environmental information 408 and use it to create new rules during a time frame that the brain-aware personalization and recommendation engine 432 is also in operation.

Although FIG. 4 illustrates an example of a contextual neurofeedback system, various changes may be made to FIG. 4. For example, various components in FIG. 4 could be combined, further subdivided, or omitted and additional components could be added according to particular needs. As a particular example, the smart and sampler 410, brain wave discretizer 412, and brain state analysis module 416 may be combined into one module.

Figure 5:
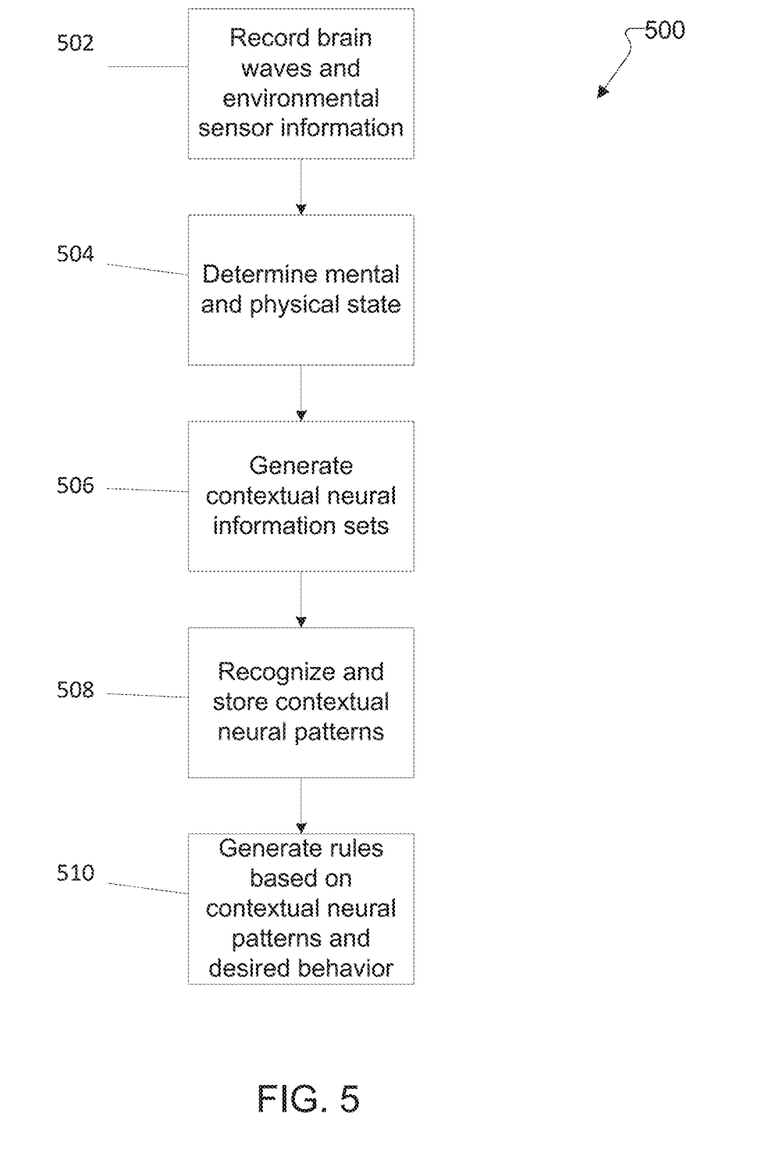
FIG. 5 illustrates a flow diagram of an example method for generating a model of contextual neural patterns of a user according to illustrative embodiments of the present disclosure.

FIG. 5 illustrates a flow diagram of an example method 500 for generating a model of contextual neural patterns of a user according to illustrative embodiments of the present disclosure. The method 500 may, for example, be performed by one of or any combination of a server 104, a smartphone 106, a scanning device 112, computer system 200, or any appropriate electronic device 300. For simplicity, the method 500 will be described as performed by an electronic device 300.

Beginning at block 502, the electronic device 300 records a user 110's brain waves as well as environmental information from the user 110's environment 114. This information may be gathered as described above, for example by sensors 365 in electronic device 300. In some embodiments, this information is gathered by sensors in other electronic devices 300, and is transmitted to the electronic device 300 that is performing the method 500.

At block 504, the electronic device 300 analyzes the recorded brain waves and environmental information to determine the user 110's mental state and physical state as described above. For example, the electronic device 300 may determine based on frequency of recorded brain waves that the user 110 was experiencing Theta waves, from which the electronic device 300 may deduce that the user 110 was bored. The electronic device 300 may also, for example, determine that the user's facial expression during this timeframe was indicative of boredom or frustration, and that the user was driving at 30 miles per hour in a car with an internal temperature of 75 degrees Fahrenheit while listening to a low tempo music track on the car's audio system. In some embodiments, some or all of this analysis may be performed remotely, for example on a server 104 or another electronic device 300, and the results returned to the electronic device 300 for future use.

At block 506, electronic device 300 generates contextual neural information sets, as described above, from the results of the analysis at block 504. This may be done by associating mental state information, physical state information, and environmental information that were recorded during a similar timeframe. In this way, the electronic device 300 builds up a database of information on the user 110's mental and physical states in various environmental contexts.

At block 508, the electronic device 300 recognizes contextual neural patterns from the sets of contextual neural information as described above. For example, the electronic device 300 may search for sets of mental and physical state information that are similar, and compare the environmental information that is part of the same contextual neural information sets as the mental and physical states. The electronic device 300 may, in this way, learn how the user 110 mentally and physically reacts to environmental contexts. During this process, the electronic device 300 may be able to determine confidence values associated with the mental and physical reactions to given environmental contexts. For example, the electronic device 300 may find that 70% of the time when the user 110 hears a specific song (e.g., a high tempo song) under specific circumstances (e.g., driving 20-40 miles per hour at 5:00-6:00 PM) they become excited and engaged, and the remaining 30% of the time they experience no change in mental or physical state.

At block 510, the electronic device may generate rules of behavior based on the contextual neural patterns detected in block 508. In some embodiments, these rules of behavior may be designed to modify the behavior of the electronic device 300 itself, the behavior of other electronic devices 300, or the behavior of other appropriate devices in the user 110's environment 114. The electronic device 300 may generate rules to achieve various desired results, for example relaxing a user who is in an agitated state, exciting a user who is in a bored state, further relaxing of a user that is entering a relaxed state, or the like. Continuing the example of block 508, the electronic device 300 may recognize that the user 110 is driving in rush hour traffic, and that the user 110 is bored and frustrated. The electronic device 300 may generate a rule to be applied in this scenario that will result in the user being more focused.

For example, a rule may be generated that instructs a smartphone 106 or a vehicle audio system to play one of a specific set of music tracks that are high tempo and instructs a vehicle climate control system to reduce the temperature to 68 degrees Fahrenheit. In some embodiments, generated rules are associated with an expected result (e.g., user 110 will become excited and engaged) and a confidence value of that result (e.g., 70% chance of result occurring). Generated rules are stored for later use.

Figure 6:
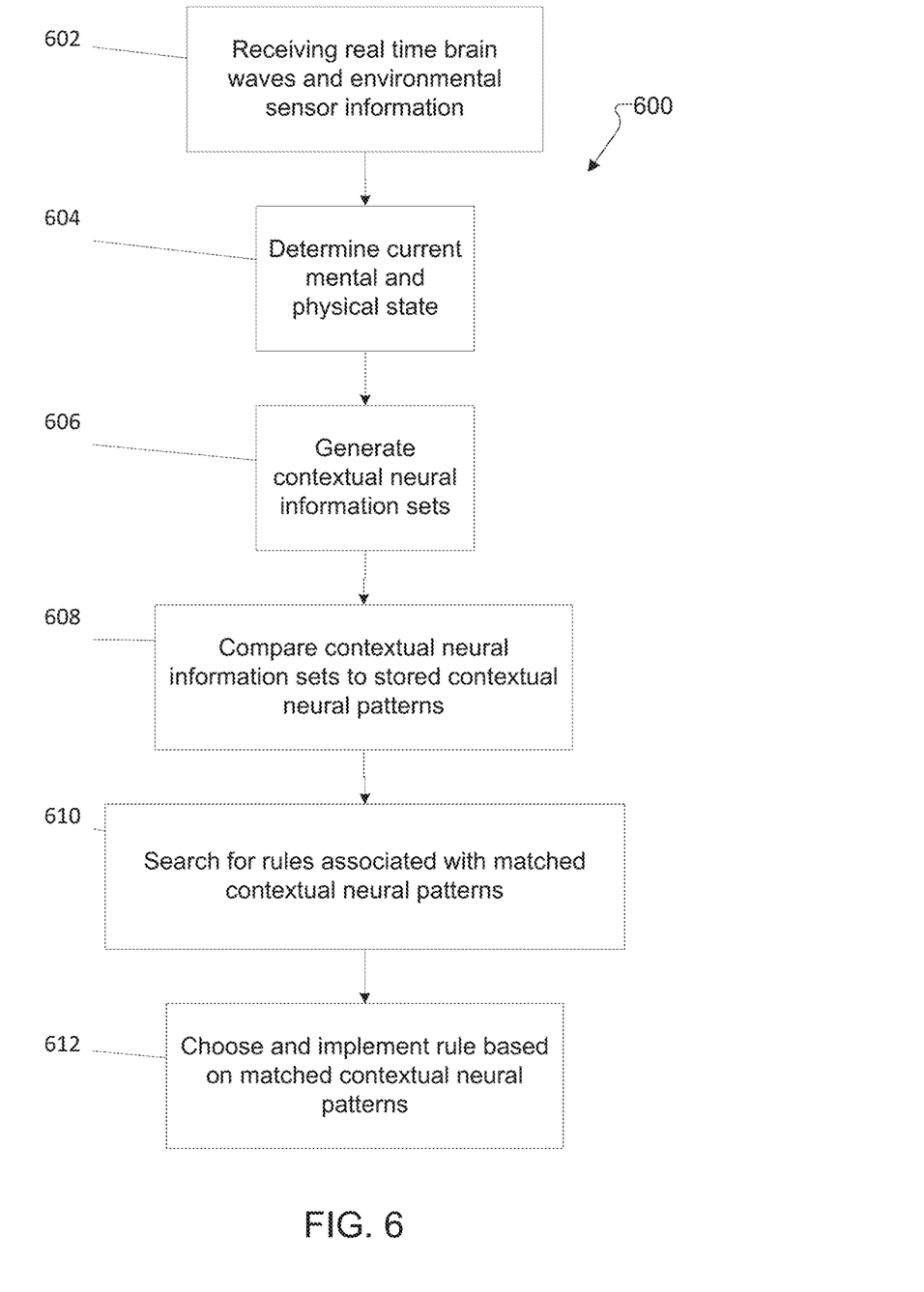
FIG. 6 illustrates a flow diagram of an example method for detecting real time mental and physical states of a user as well as real time environmental information about the user's environment and, based on the environmental information, implementing a rule to modify the behavior of one or more electronic devices according to illustrative embodiments of the present disclosure.

FIG. 6 illustrates a flow diagram of an example method 600 for detecting real time mental and physical states of a user 110 as well as real time environmental information about the user 110's environment 114 and, based on the environmental information, implementing a rule to modify the behavior of one or more electronic devices according to illustrative embodiments of the present disclosure. The method 600 may, for example, be performed by one of or any combination of a server 104, a smartphone 106, a scanning device 112, computer system 200, or any appropriate electronic device 300. For simplicity, the method 600 will be described as performed by an electronic device 300.

Beginning at block 602, the electronic device 300 receives in real time a user 110's brain waves as well as environmental information from the user 110's environment 114. This information may be gathered as described above, for example by sensors 365 in electronic device 300. In some embodiments, this information is gathered by sensors in other electronic devices 300, or by any other appropriate device, and is transmitted to the electronic device 300 that is performing the method 600.

At block 604, the electronic device 300 analyzes the real time brain waves and real time environmental information, as described above, to determine the user 110's real time mental state and physical state. For example, the electronic device 300 may determine that the user 110 is currently experiencing Theta waves, and the electronic device 300 may deduce that the user 110 is bored. The electronic device 300 may also, for example, determine that the user's facial expression is indicative of boredom or frustration, and that the user is driving at 20 miles per hour in a car with an internal temperature of 73 degrees Fahrenheit while listening to a medium tempo music track on the car's audio system. In some embodiments, some or all of this analysis may be performed remotely, for example on a server 104 or another electronic device 300, and the results returned to the electronic device 300 for use.

At block 606, the electronic device 300 generates contextual neural information sets from the results of the analysis at block 604 as described above. This may be done by associating real time mental state information, physical state information, and environmental information with each other.

At block 608, the electronic device 300 compares the contextual neural information sets formed in block 606 with stored contextual neural patterns such as those generated by method 500 as described above. Continuing the example of block 604, the electronic device 300 may search for contextual neural patterns that are characterized by Theta waves, a bored or frustrated facial expression, driving at a speed near 20 miles per hour (e.g., 15-35 miles per hour) with internal temperature of the vehicle near 73 degrees Fahrenheit (e.g., 71-75 degrees Fahrenheit), and music playing with a tempo around a medium tempo. In some embodiments, contextual neural patterns may be considered a match when only some of the pieces of data match the real time data. Contextual neural patterns that match less than all pieces of data may be given a lower weight than contextual neural patterns that match all pieces of data. Similarly, contextual neural patterns may be given a weight based on how closely each piece of data matches (e.g., the closer the match the higher the weight).

At block 610, the electronic device 300 searches for rules based on the matched contextual neural patterns. For example, the electronic device 300 may use a rule matching engine 438 as described above to search for rules. Continuing the example of block 608, the result of the rule search based on the real time contextual neural patterns may be a rule that contains instructions to play one of a specific set of music tracks that are high tempo and to reduce the internal temperature of a vehicle cabin to 68 degrees Fahrenheit. In some embodiments, more than one rule may result from the search, and a user 110 may be prompted by the electronic device to select one of them for implementation as described below. In other embodiments, a rule may be selected automatically (either by the electronic device 300 or another device that implements the rule matching function), for example based on the confidence value of expected results and based on the weight assigned to each matched contextual neural pattern in block 608 (e.g., lower weighted contextual neural pattern matches may have their associated rules weighted lower as well).

At block 612 the electronic device 300 implements a rule resulting from the search at block 610. Continuing with the example of block 610, the electronic device 300 finds a rule that contains instructions to play one of a specific set of music tracks that are high tempo and to reduce the internal temperature of a vehicle cabin to 68 degrees Fahrenheit.

Accordingly, in the case that the electronic device 300 is a smartphone 106, the electronic device 300 changes the track of a music app running on the smartphone 106 to a high tempo selection and communicates with a smart vehicle control system to adjust the internal temperature to 68 degrees Fahrenheit.

Embodiments of the present disclosure provide systems and methods for fusion of brain wave information and sensed environmental context information to create rules for personalization of the settings of one or more electronic devices, or rules for providing recommendations for settings of one or more electronic devices. For example, embodiments of the present disclosure describe recording brain wave and contextual environmental context information, correlating the brain wave and contextual environmental context information to determine the mental reactions of a user to environmental stimuli, and use that determination to form rules for modifying the settings of one or more electronic devices to modify the environment of the user to induce desired mental reactions.

Embodiments of the present disclosure also provide systems and methods for receiving real time brain wave and contextual environmental context information, correlating the real time brain wave and contextual environmental context information, and using that information to search for rules that will modify the environment of the user to induce desired mental reactions.

Although the present disclosure has been described with an exemplary embodiment, various changes and modifications may be suggested to one skilled in the art. It is intended that the present disclosure encompass such changes and modifications as fall within the scope of the appended claims.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

What is claimed is:

1. A method for a neural feedback system, comprising:
   receiving, from one or more sensors, a plurality of brain waves of a user;
   recording the plurality of brain waves of the user;
   recording sensor data measuring at least one of a physical state or an activity of the user;
   comparing the recorded brain waves and the recorded sensor data against a context-based brain wave information of the user, the context-based brain wave information comprising neural information corresponding to respective environmental condition information;
   updating the context-based brain wave information of the user based on correlations between the recorded brain waves and the recorded sensor data;
   identifying context-based brain wave patterns in the context-based brain wave information of the user;
   associating at least one rule of at least one electronic device with at least one recorded context-based brain wave pattern;
   identifying a mental state of the user based on a comparison of the recorded context-based brain wave patterns and the brain waves of the user;
   predicting a change in at least one a mental or physical state of the user in response to current environmental conditions; and
   controlling, in response to the identified mental state of the user and a current activity of the user, at least one electronic device to perform at least one function according to the at least one rule to alter the mental state of the user.

2. The method of claim 1, further comprising generating the context-based brain wave information for the user based on correlations between previous environmental information, previous brain waves of the user, and at least one of a previous physical state of the user or a previous activity of the user.

3. The method of claim 1, wherein:
   the sensor data is recorded in a first time frame,
   the brain waves are recorded in a second time frame, and
   the first and second time frames overlap at least partially.

4. The method of claim 2, further comprising prior to generating the context-based brain wave information:
   sampling the recorded brain waves efficiently to generate sampled recorded brain waves; and
   discretizing the sampled recorded brain waves and the recorded sensor data.

5. The method of claim 1, wherein identifying the mental state of the user further comprises:
   receiving brain waves of the user in real time;
   receiving data related to at least one of a physical state or an activity of the user in real time;
   generating real time context-based brain wave information by detecting correlations between the sensed brain waves and the sensed data; and
   determining whether the real time context-based brain wave information is similar to at least one of the recorded context-based brain wave patterns, wherein the at least one of the recorded context-based brain wave patterns has at least one associated rule.

6. The method of claim 5, further comprising, in response to determining that the real time context-based brain wave information is similar to at least one of the context-based brain wave patterns, causing the at least one electronic device to receive the at least one rule associated with the at least one of the recorded context-based brain wave patterns.

7. The method of claim 1, wherein controlling the at least one electronic device comprises causing an external electronic device to perform the at least one function according to the at least one rule.

8. The method of claim 1, wherein identifying the mental state is performed by the at least one electronic device, and wherein controlling at least one electronic device comprises, causing the at least one electronic device to perform the at least one function according to the at least one rule.

9. The method of claim 1, further comprising:
   determining a known neural response to the rule based on context-based brain wave patterns of the user that were formed while previously performing the rule;
   determining a confidence value of a desired result of the known neural response of the user, wherein the confidence value is associated with a probability of occurrence of the desired result of the known neural response of the user; and
   determining the at least one rule to associate with each context-based brain wave pattern based on the known neural response and the confidence value.

10. A neural feedback system, comprising:
    one or more sensors; and
    a processor configured to:
    receive, from the one or more sensors, recorded brain waves of a user;

receive, from the one or more sensors, recorded sensor data measuring at least one of a physical state or an activity of the user;

compare the recorded brain waves and the recorded sensor data against a context-based brain wave information of the user, the context-based brain wave information comprising neural information corresponding to respective environmental condition information;

update the context-based brain wave information of the user based on correlations between the recorded brain waves and the recorded sensor data;

identify context-based brain wave patterns in the context-based brain wave information of the user;

associate at least one rule of at least one electronic device with at least one recorded context-based brain wave pattern;

identify a mental state of the user based on a comparison of the recorded context-based brain wave patterns and the brain waves of the user;

predicting a change in at least one a mental or physical state of the user in response to current environmental conditions; and control, in response to the identified mental state of the user and a current activity of the user, at least one electronic device to perform at least one function according to the at least one rule to alter the mental state of the user.

11. The neural feedback system of claim 10, further comprising a memory configured to store the context-based brain wave information.

12. The neural feedback system of claim 10, wherein:
the sensor data is recorded in a first time frame,
the brain waves are recorded in a second time frame, and
the first and second time frames overlap at least partially.

13. The neural feedback system of claim 10, the processor further configured to, prior to updating of the context-based brain wave information, generate the context-based brain wave information by:

sampling the recorded brain waves efficiently to generate sampled recorded brain waves; and discretizing the sampled recorded brain waves and the recorded sensor data.

14. The neural feedback system of claim 10, wherein to identify the mental state of the user, the processor further configured to:

receive brain waves of the user in real time;

receive data related to at least one of a physical state or an activity of the user in real time;

generate real time context-based brain wave information by detecting correlations between the sensed brain waves and the sensed data; and determine whether the real time context-based brain wave information is similar to at least one of the recorded context-based brain wave patterns, wherein the at least one of the recorded context-based brain wave patterns has at least one associated rule.

15. The neural feedback system of claim 14, the processor further configured to, in response to determining that the real time context-based brain wave information is similar to at least one of the context-based brain wave patterns, cause the at least one electronic device to receive the at least one rule associated with the at least one of the recorded context-based brain wave patterns.

16. The neural feedback system of claim 10, wherein, to control the at least one electronic device, the processor is configured to cause at least one external electronic device to perform the at least one function according to the at least one rule.

17. The neural feedback system of claim 10, wherein, to control the at least one electronic device, the processor is configured to perform the at least one function according to the at least one rule.

18. The neural feedback system of claim 10, the processor further configured to:

determine a known neural response to the rule based on context-based brain wave patterns of the user that were formed while previously performing the rule;

determine a confidence value of a desired result of the known neural response of the user, wherein the confidence value is associated with a probability of occurrence of the desired result of the known neural response of the user; and determine the at least one rule to associate with each context-based brain wave pattern based on the known neural response and the confidence value.

19. A non-transitory computer readable medium embodying a computer program, the computer program comprising computer readable program code that, when executed by at least one processor in an electronic device, causes the at least one processor to:

record a plurality of brain waves of a user;

record sensor data measuring at least one of a physical state or an activity of the user;

compare the recorded brain waves and the recorded sensor data against a context-based brain wave information of the user, the context-based brain wave information comprising neural information corresponding to respective environmental condition information;

update the context-based brain wave information of the user based on correlations between the recorded brain waves and the recorded sensor data;

identify context-based brain wave patterns in the context-based brain wave information of the user;

associate at least one rule of at least one electronic device with at least one recorded context-based brain wave pattern;

identify a mental state of the user based on a comparison of the recorded context-based brain wave patterns and the brain waves of the user;

predict a change in at least one a mental or physical state of the user in response to current environmental conditions; and control, in response to the identified mental state of the user and a current activity of the user, at least one electronic device to perform at least one function according to the at least one rule to alter the mental state of the user.

20. The non-transitory computer readable medium of claim 19, wherein the computer readable program code, when executed, causes the at least one processor to generate the context-based brain wave information for the user based on correlations between previous brain waves of the user and at least one of a previous physical state of the user or a previous activity of the user.

21. The non-transitory computer readable medium of claim 19, wherein:
the sensor data is recorded in a first time frame,
the brain waves are recorded in a second time frame, and
the first and second time frames overlap at least partially.

22. The non-transitory computer readable medium of claim 20, wherein the computer readable program code, when executed, causes the at least one processor to, prior to generation of the context-based brain wave information:
    sample the recorded brain waves efficiently to generate sampled recorded brain waves; and
    discretize the sampled recorded brain waves and the recorded sensor data.

23. The non-transitory computer readable medium of claim 19, wherein to identify the mental state of the user, the computer readable program code, when executed, causes the at least one processor to:
    receive brain waves of the user in real time;
    receive data related to at least one of a physical state or an activity of the user in real time;
    generate real time context-based brain wave information by detecting correlations between the sensed brain waves and the sensed data; and
    determine whether the real time context-based brain wave information is similar to at least one of the recorded context-based brain wave patterns,
    wherein the at least one of the recorded context-based brain wave patterns has at least one associated rule.

24. The non-transitory computer readable medium of claim 23, wherein the computer readable program code, when executed, causes the at least one processor, cause, in response to determining that the real time context-based brain wave information is similar to at least one of the context-based brain wave patterns, the at least one electronic device to receive the at least one rule associated with the at least one of the recorded context-based brain wave patterns.

25. The non-transitory computer readable medium of claim 19, wherein to control the at least one electronic device, the computer readable program code, when executed, causes the at least one processor to cause an external electronic device to perform the at least one function according to the at least one rule.

26. The non-transitory computer readable medium of claim 19, wherein to control the at least one electronic device, the computer readable program code, when executed, causes the at least one processor to cause the electronic device to perform the at least one function according to the at least one rule.

27. The non-transitory computer readable medium of claim 19, wherein the computer readable program code, when executed, causes the at least one processor to:
    determine a known neural response to the rule based on context-based brain wave patterns of the user that were formed while previously performing the rule;
    determine a confidence value of a desired result of the known neural response of the user, wherein the confidence value is associated with a probability of occurrence of the desired result of the known neural response of the user; and
    determine the at least one rule to associate with each context-based brain wave pattern based on the known neural response and the confidence value.

\* \* \* \* \*